United States Patent

Thiele et al.

Patent Number: 4,603,204
Date of Patent: Jul. 29, 1986

[54] THEOPHYLLINE DERIVATIVES

[75] Inventors: Kurt Thiele; Felix Geissmann; Ludwig Zirngibl; Ulrich Jahn, all of Zofingen, Switzerland

[73] Assignee: Siegfried Aktiengesellschaft, Zofingen, Switzerland

[21] Appl. No.: 474,230

[22] Filed: Mar. 11, 1983

[30] Foreign Application Priority Data

Jul. 20, 1981 [CH] Switzerland .................. 4739/81

[51] Int. Cl.⁴ .................. C07D 473/08; A61K 31/52
[52] U.S. Cl. .................. 544/267; 544/268; 544/269
[58] Field of Search .................. 544/268, 270, 269; 424/253; 514/265

[56] References Cited

U.S. PATENT DOCUMENTS

| | | | |
|---|---|---|---|
| 3,642,798 | 2/1972 | Nitta et al. | 544/270 |
| 4,086,347 | 4/1978 | Friebe et al. | 424/253 |
| 4,400,381 | 8/1983 | Favier et al. | 424/253 |
| 4,548,820 | 10/1985 | Legnier et al. | 514/265 |
| 4,548,939 | 10/1985 | Dennis et al. | 514/265 |

Primary Examiner—Nicholas S. Rizzo
Attorney, Agent, or Firm—Jordan and Hamburg

[57] ABSTRACT

New derivatives of theophylline having the formula

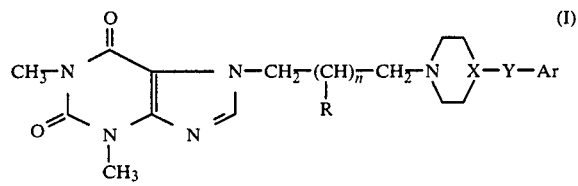

in which R denotes hydrogen or OH, n the numbers 0 or 1, X either >CH— or >N—, Y either —O— or —CO— and R a five membered or six membered aryl ring or hetero-aryl ring, that is substituted in given cases with halogen, short chain alkyl groups, alkoxy groups or halogen-alkyl, and exhibit in addition to other properties, histamine-, serotinine- bradykynine- antagonistic, anti-anaphylactic and -adrenergic stimulating effects.

3 Claims, No Drawings

THEOPHYLLINE DERIVATIVES

The invention relates to new derivatives of theophylline, having the formula

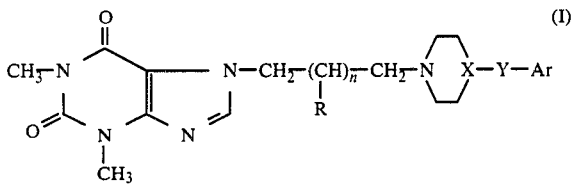

and their pharmaceutically acceptable, acid-addition salts.

In the above formula:
R is hydrogen or the hydroxy group,
n is the numbers 0 or 1,
X is >CH— or >N—,
Y is —O— or

and Ar denotes a five- or six-member carbocyclic or hetereocyclic aromatic unsaturated ring, in given cases substituted with a short-chain alkyl or short-chain alkoxy-group of 1 to 3 C-atoms, preferably methyl-groups, substituted by halogens, particularly fluorine, chlorine or bromine, preferably fluorine, or substituted by methyl-halide, as for instance trifluoromethyl, said rings being particularly phenyl-, pyridyl-, furyl-, thienyl-, pyrrolyl or imidazolyl-rings, preferably phenyl- or furyl-rings.

These compounds may be prepared according to the process that is also the subject of the invention, said process being characterized by reacting a theophylline which is substituted in the 7-position with a group of the formula:

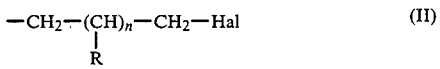

(where R and n denote the same as in the aforenamed formula (I) and where "Hal" denotes chlorine or bromine) with a base of formula

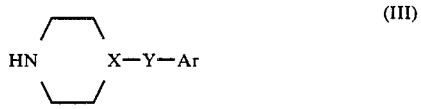

The reaction may be initiated at elevated temperature with or without the use of a solvent (isopropanol, for instance). When operating without a solvent, the base materials are held at the temperature of a molten mixture, until periodically taken samples of the reaction mixture show by thin layer chromatography that the reaction is substantially finished. In that case, one advantageously uses the base as an initial material of formula (III) in double or triple excess for binding the split-off hydrogen halide.

The starting materials of formula (II) are known and may be easily obtained; when so desired, they may be synthesized in a known manner (see Arzneim.-Forsch. 27,5 ff. (1977)) by condensation of theophylline with the respective alkylene dihalides or epichlorhydrin, respectively. The bases of the formula (III) may also be obtained as commercial products in the form of their hydrochloride-salts, from which they may be liberated by treatment with alkali metal hydroxides in a manner known to the expert prior to their use for the reaction according to the invention.

It has been shown that the derivatives of theophylline according to the invention surprisingly exhibit versatile pharmacological effects.

The pharmacodynamical properties of the derivatives of xanthine have caused the pharmaceutical industry to also study intensively theophylline and its derivatives because of their influence upon the heart and the circulation. At the turn of the century, one already began to substitute the theophylline-molecule with basic groups in order to counteract its low solubility in water, and as a consequence, a large number of theophylline derivatives have been synthesized, some with hydrophylic substituents in the 7-position, or some in the form of addition- or double salts. Many of these have found their place as medical substances in therapy, where direct or indirect use was made of their advantageous influence upon circulation, in order to use them as vaso-, coronary, bronchio-dilators or antiasthmatics, as long as they are not salts or double-salts or similar substances, whose additive ions or molecular components (as, for instance in the case of ephedrine) exhibit specific individual components of effect and in that sense include additive components of effect or may even overshadow and dominate the effect of theophylline.

Recently 7-(4-aminopiperidino-propyl)-theophyllines with antiallergic and antihistamic effects have been described in DE-OS No. 29 22 159. In similar direction, the substances according to the invention were also shown to have, in addition to other activities, outstanding histamine-, serotonine- and bradykinine-, antagonistical, blood pressure lowering, antianaphylactical and β-adrenergic stimulating properties and which distinctly differ by this broad spectrum of activity from the conventional derivatives of theophylline. Based upon the aforementioned pharmacodynamical properties, therapeutical use can be found as migraine remedies, broncholytics, antiallergenics, antiphylogistics, analgesics and antihypertonics. The substances having the codes Sgd 195-78 (see the following example 2) and Sgd 144-80 (see example 3) were especially promising. Thus, according to current knowledge, those compounds of formula (I) may be favored, where R denotes a hydrogen atom, n the number 0 or 1 (preferably 0), X the methylene group, Y the keto group and Ar a parasubstituted phenyl group, particularly the p-fluorine-phenyl group.

In the structural formulae of the following examples, "Th" denotes the theophylline group, which is bound in the 7-position to the partial structure mentioned in the individual example.

EXAMPLE 1

7-[2-[4-(p-tolyloxy)-piperidine]-ethyl]-theophylline (Sgd 94-78)

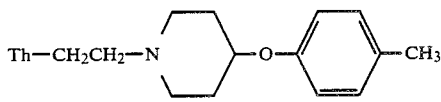

2.4 g (0.01 Mol) 7-(2-chloroethyl)-theophylline) is carefully mixed with 3.8 g (0.02 Mol) 4-(p-tolyloxy)-piperidine while solid and heated in a round flask upon an oil bath at a bath temperature of 90° C. A clear melt soon results, whereupon the mixture solidifies after approximately 15 minutes. The mass is further maintained at the same temperature until thin layer chromatography (CHCl$_3$+10% methanol) shows that the reaction has ended. That occurs after about 6 hours. The mass is allowed to cool, mixed with water and extracted with chloroform. The chloroform is distilled off after drying of the extract with MgSO$_4$. The residue is recrystallized in isopropanol and presently yields 3.0 g of a product with a mp of 121°-122° C.

$C_{21}H_{27}N_5O_3$: 397.47: cal. C 63.62; H 6.61; N 17.66; O 12.11; Fd. C 62.75; H 6.96; N 17.42; O 13.02

The 7-(2-chloroethyl)-theophylline used as a starting material is known and may be prepared by the reaction of theophylline with ethylene dichloride. The 4-(p-tolyloxy)-piperidine, used as free base may be obtained by treating the respective hydrochloride with sodium hydroxide solution.

EXAMPLE 2

7-[2-[4-(p-fluorobenzoly)-piperidino]-ethyl]-theophylline (Sgd 195-78)

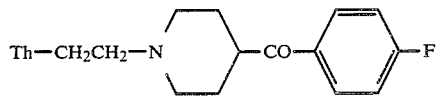

25.6 g (0.124M) 4-(p-fluorobenzoyl)-piperidine is heated together with 15.0 g (0.062M) 7-(2-chloroethyl)-theophylline in the solid state in a round flask to 100° C. during one hour. It is cooled down to 60° C. and ethyl acetate is added while stirring until a homogeneous suspension is present. After cooling and filtering off of the separated fluorobenzoylpiperidine hydrochloride, 2n hydrochloric acid is added to the filtrate for the precipitation of the raw product. The residue, separated by filtration, is washed twice, each time with water and ethyl acetate, and subsequently a layer of ethyl acetate is added and 100 ml sodium hydroxide solution is added. After agitation and separation of the phases, the principal amount of the product resides in the organic phase; in order to obtain additional amounts of product, the aqueous phase is shaken twice, each with 100 ml ethyl acetate. The combined organic phases are washed with saturated NaCl solution, treated with activated carbon, dried over MgSO$_4$ and filtered. After distilling off of the solvent, the filtrate yields 20.4 g (80%) raw crystalline product. For additional purification, the residue is suspended in 250 ml carbon tetrachloride and heated at reflux temperature. The dark brown solution obtained thereby, becomes light orange after treatment with activated carbon and on cooling yields 14.5 g white product with an mp of 143°-145° C., which is shown to be pure by thin layer chromatography.

$C_{21}H_{24}FN_5O_3$: 413.46: calc. C 61.00; H 5.85; N 16.94; F 4.60; fd. C 60.80; H 5.66; N 17.11; F 4.46

A pure product of identical composition according to thin layer chromatography which melts under decomposition at 248° C. was obtained by heating the starting materials mixed at the same ratio to 120° C. for five hours, subsequently boiling 7 hours in n-propanol, corresponding working-up and crystallizing from carbon tetrachloride.

calc. C 61.00; H 5.85; N 16.94; F 4.60; fd. C 60.53; H 5.63; N 16.49; F 4.06

EXAMPLE 3

7-[3-[4-(p-fluorobenzoyl)-piperidino]-propyl]-theophylline (Sgd 144-80)

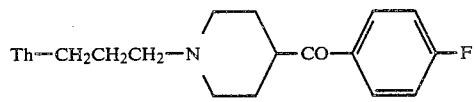

10.2 g 4-(p-fluorobenzoyl)-piperidine and 16.5 g 7-(chloropropyl)-theophylline are carefully mixed in the solid state and heated to 100° C. in a round flask in an oil bath. The mixture at first results in a clear melt, subsequently begins to crystallize and then changes into a solid mass. It is allowed to cool after 10 minutes, dissolved in ethyl acetate and 2n hydrochloric acid is added, whereby a dark oil separates in the organic phase, crystallizing on standing overnight. By recrystallizaing with 100 ml carbon tetrachloride, an intially oily then crystallizing substance is obtained, 7.4 g of the product with an mp of 114° to 119° C. (yield: 43.5%)

$C_{22}H_{26}FN_5O_3$: 427.5; calc. C 61.81; H 6.13; N 16.38; F 4.45; fd. C 61.90; H 6.01; N 16.40; F 4.29

The 7-(3-chloropropyl)-theophylline, used as a starting material, may be obtained in a known manner, for instance by the reaction of theophylline with 1,3-bromo-chloropropane.

EXAMPLE 4

7-[3-[4-(p-fluorobenzoyl)-piperidino]-2-hydroxypropyl]-theophylline hydrate (Sgd 145-80)

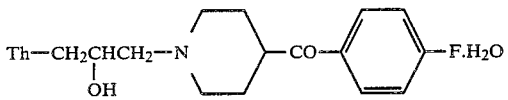

8 g 7-(3-chloro-2-hydroxypropyl)-theophylline, mixed with 12.16 g 4-(fluorobenzoyl)-piperidine are maintained for 1 hour in an oil bath at a temperature of 100° C., whereby the viscosity of the melt, which is initially highly fluid and clear, rises after 30 minutes. After cooling, the mixture is treated for 30 minutes with ethyl acetate while being vigorously stirred. The solution, thereby produced, is separated by filtering, from the separated 4-(p-fluorobenzoyl)-piperidine hydrochloride, and 2n hydrochloric acid is added. After phase separation, the aqueous phase is shaken with ethyl acetate, made alkaline by the addition of concentrated sodium hydroxide solution and extracted twice with ethyl acetate. The substance crystallizing from the extract exhibits a melting point of 132°-138° C. after recrystallization from chloroform-ethanol (9:1) and drying in a high vacuum.

$C_{22}H_{26}FN_5O_4 \cdot H_2O$: 461.5; calc. C 57.26; H 6.12; N 15.18; F 4.12; fd. C 57.54; H 6.15; N 15.52; F 4.10

The 7-(3-chloro-2-hydroxpropyl)-theophylline may be prepared in a known manner by the reaction of theophylline and epichlorohydrin.

EXAMPLE 5

7-[3-[4-(2-furoyl)-1-piperazinyl]-2-hydroxypropyl]-theophylline (Sgd 269-76)

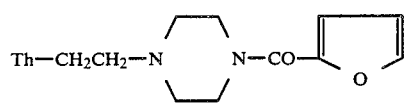

A mixture of 2 g (8.26 mMol) 7-(2-chloro-ethyl)-theophylline and 3.78 g (21 mMol) N-furoyl piperazine is melted at 100° C. upon an oil bath and held for 3 hours at that temperature. After cooling, the solidified mass is dissolved in methylene chloride. The solution is extracted with water and subsequently shaken twice with 10% hydrochloric acid. The combined aqueous phases are made alkaline with sodium hydroxide solution and again extracted with methylene chloride and the resulting extract is dried over MgSO₄ and concentrated. The residue is washed twice with water at 60° C. and again dissolved in methylene chloride. The solution is dried over MgSO₄, relieved of solvent by evaporation, and recrystallized in ethyl acetate, yielding the pure product having a melting point of 142°–144° C.

$C_{18}H_{22}N_6O_4$: 386.41: calc. C 55.95; H 5.74; N 21.75; fd. C 55.86; H 5.84; N 21.71

EXAMPLE 6

7-[3-[4-(2-furoyl)-1-piperazinyl]-hydroxypropyl]-theophylline (Sgd 123-77)

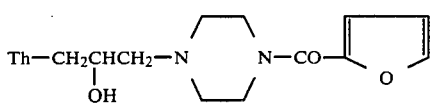

A mixture of 4 g 7-(3-chloro-2-hydroxypropyl)-theophylline with 6.6 g N-(2-furoyl)-piperazine is heated one hour to 120° C.; the reaction mixture is dissolved in chloroform and extracted with water. The organic phase is dried over MgSO₄ and concentrated by evaporation; the residue is recrystallized from isopropanol and results in 2.8 g of a product having a melting point of 161°–163° C.

$C_{19}H_{24}N_6O_5$: 416.44: calc. C 54.80; H 5.81; N 20.18; O 19.12; fd. C 54.66; H 6.01; N 19.72; O 19.99

We claim:

1. A theophylline derivative of the formula

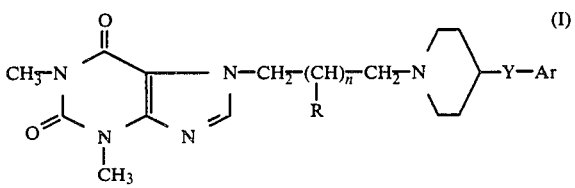

wherein
R is hydrogen or a hydroxy group
n is 0 or 1,
Y is —O— or

and Ar is a phenyl, pyridyl, furyl, thienyl, pyrrolyl or imidazolyl ring which is unsubstituted or substituted with a methyl group, fluorine, chlorine, bromine, or trifluoromethyl.

2. The compound of claim 1 wherein Ar is a furyl ring, or a phenyl ring which is substituted with a methyl group or fluorine.

3. The compound of claim 1 which is 7-(2-(4-(p-tolyloxy)piperidino)-ethyl)theophylline.

* * * * *